(12) United States Patent
Amisano et al.

(10) Patent No.: US 11,049,599 B2
(45) Date of Patent: Jun. 29, 2021

(54) ZERO KNOWLEDGE MULTI-PARTY PRESCRIPTION MANAGEMENT AND DRUG INTERACTION PREVENTION SYSTEM

(71) Applicant: INTERNATIONAL BUSINESS MACHINES CORPORATION, Armonk, NY (US)

(72) Inventors: Michael A. Amisano, East Northport, NY (US); John F. Behnken, Hurley, NY (US); Jeb R. Linton, Manassas, VA (US); John L. Melchionne, Kingston, NY (US); David K. Wright, Riverview, MI (US)

(73) Assignee: International Business Machines Corporation, Armonk, NY (US)

( * ) Notice: Subject to any disclaimer, the term of this patent is extended or adjusted under 35 U.S.C. 154(b) by 106 days.

(21) Appl. No.: 16/004,336

(22) Filed: Jun. 8, 2018

(65) Prior Publication Data
US 2019/0378599 A1    Dec. 12, 2019

(51) Int. Cl.
*G16H 20/10* (2018.01)
*G06F 16/951* (2019.01)
*G16H 10/60* (2018.01)

(52) U.S. Cl.
CPC .......... *G16H 20/10* (2018.01); *G06F 16/951* (2019.01); *G16H 10/60* (2018.01)

(58) Field of Classification Search
CPC .... G06F 1/00–2221/2153; G16H 10/00–80/00
See application file for complete search history.

(56) References Cited

U.S. PATENT DOCUMENTS 6,529,892 B1 * 3/2003 Lambert ............... G06F 40/226
                                                706/55
7,072,840 B1   7/2006 Mayaud
(Continued)

FOREIGN PATENT DOCUMENTS

WO    WO-2015066523 A2 *  5/2015 ......... G06F 21/6254

OTHER PUBLICATIONS

Anonymous, "System and Method for Drug Interaction Validation," An IP.com Prior Art Database Technical Disclosure, Aug. 17, 2016, p. 1, IP.com No. IPCOM000247242D.
(Continued)

*Primary Examiner* — Elaine Gort
*Assistant Examiner* — Jonathon A. Szumny
(74) *Attorney, Agent, or Firm* — Dmitry Paskalov (57) ABSTRACT

A method for implementing a secure system to prevent adverse drug interactions and repeat prescriptions, for a patient, in a multi-party computing environment. The method includes receiving a patient identifier from a provider, authenticating an access by the provider, and retrieving a second patient identifier, wherein the second patient identifier corresponds to the received patient identifier, wherein the received patient identifier and the second patient identifier are different. The method further includes receiving an input from the provider that corresponds to the patient identifier, and accessing a database that contains a stored private ID, wherein the stored private ID is a combination of the received patient identifier and the retrieved second patient identifier, and wherein the database includes data relating to the patient. The method includes searching the database to obtain a search result based on the received input from the provider, and transmitting the search result to the provider.

16 Claims, 6 Drawing Sheets

(56) References Cited

U.S. PATENT DOCUMENTS

| | | | |
|---|---|---|---|
| 9,973,484 B2* | 5/2018 | Reid | H04L 63/061 |
| 10,366,462 B1* | 7/2019 | Miller | G06Q 50/22 |
| 2003/0050802 A1 | 3/2003 | Jay et al. | |
| 2003/0074225 A1 | 4/2003 | Borsand et al. | |
| 2004/0172307 A1 | 9/2004 | Gruber | |
| 2005/0236474 A1* | 10/2005 | Onuma | G06F 21/6227 235/382 |
| 2006/0149416 A1 | 7/2006 | Mohapatra et al. | |
| 2007/0047770 A1* | 3/2007 | Swope | A61B 5/1171 382/115 |
| 2008/0288287 A1* | 11/2008 | Stanners | G06F 19/326 705/2 |
| 2008/0304663 A1* | 12/2008 | Canard | G06F 21/6254 380/45 |
| 2009/0106313 A1 | 4/2009 | Boldyga | |
| 2010/0169218 A1 | 7/2010 | Wang et al. | |
| 2010/0241595 A1* | 9/2010 | Felsher | G06F 19/328 705/400 |
| 2011/0123027 A1* | 5/2011 | Gotthardt | G06F 21/606 380/270 |
| 2012/0303616 A1* | 11/2012 | Abuelsaad | G06F 21/6227 707/736 |
| 2013/0010950 A1* | 1/2013 | Kerschbaum | H04L 9/008 380/30 |
| 2014/0058742 A1* | 2/2014 | Chari | G16H 50/20 705/2 |
| 2015/0112316 A1* | 4/2015 | Cudak | A61M 39/04 604/890.1 |
| 2015/0161398 A1* | 6/2015 | De Cristofaro | G06F 21/60 726/26 |
| 2015/0261934 A1 | 9/2015 | Miller | |
| 2015/0317430 A1* | 11/2015 | Olson | G16B 5/00 703/11 |
| 2016/0103978 A1 | 4/2016 | Stong | |
| 2016/0352730 A1* | 12/2016 | Spagnola | H04L 63/0428 |
| 2017/0177899 A1* | 6/2017 | Ng | G06F 21/6227 |
| 2017/0344724 A1* | 11/2017 | Nockley | G06F 19/3462 |
| 2018/0159833 A1* | 6/2018 | Zhang | H04L 29/06 |
| 2018/0365446 A1* | 12/2018 | Alves De Carvalho | G06F 21/6254 |
| 2019/0130128 A1* | 5/2019 | Khassanov | H04L 63/101 |
| 2019/0198146 A1* | 6/2019 | Booth | G16H 10/60 |
| 2019/0208354 A1* | 7/2019 | Raduchel | G06F 16/24578 |
| 2019/0304574 A1* | 10/2019 | Weinstock | G16H 40/20 |
| 2019/0342270 A1* | 11/2019 | Laine | H04L 9/0643 |
| 2019/0349191 A1* | 11/2019 | Soriente | H04L 9/0861 |
| 2019/0370485 A1* | 12/2019 | Tang | G06F 16/248 |
| 2019/0392955 A1* | 12/2019 | Israeli | G06F 17/18 |

OTHER PUBLICATIONS

Anonymous, "Method and System for Enhanced Medication Management System," An IP.com Prior Art Database Technical Disclosure, Nov. 25, 2016, p. 1-4, IP.com No. IPCOM000248421D.

Anonymous, "Blockchain/Cognitive Technology Platform as an Adviser to Support Pharmacy Operations: Drug Use Management and Drug Inventory Management," An IP.com Prior Art Database Technical Disclosure, Feb. 10, 2017, p. 1-4, IP.com No. IPCOM000249234D.

De Cristofaro et al., "Practical Private Set Intersection Protocols with Linear Computational and Bandwidth Complexity," Cryptology ePrint Archive, 2009, p. 1-17, Report No. 20091491, International Association for Cryptologic Research (IACR).

El Emam et al., "A Secure Distributed Logistic Regression Protocol for the Detection of Rare Adverse Drug Events," Journal of the American Medical Informatics Association, May-Jun. 2013, p. 453-461, vol. 20, Issue 3.

IBM, "Method for Reducing Errors in Prescription and Drug Interactions by Creating a Grid Enabled Prescription Registry," An IP.com Prior Art Database Technical Disclosure, Nov. 23, 2002, p. 1, IP.com No. IPCOM000016198D.

Khemmarat et al., "Supporting Drug Prescription via Predictive and Personalized Query System," 9th International Conference on Pervasive Computing Technologies for Healthcare (PervasiveHealth), 2015, p. 9-16, ICST.

Kolesnikov et al., "Efficient Batched Oblivious PRF with Applications to Private Set Intersection," Cryptology ePrint Archive, 2016, p. 1-19, Report No. 2016/799, International Association for Cryptologic Research (IACR).

Mell et al., "The NIST Definition of Cloud Computing," National Institute of Standards and Technology, Sep. 2011, p. 1-3, Special Publication 800-145.

Nichol, "Interactive and Zero-Knowledge Proofs for Better Patient Interactions with Blockchain Technology," CIO Magazine, Sep. 1, 2016, p. 1-5, IDG Communications, Inc., https://www.cio.com/article/3112198/leadership-management/interactive-and-zero-knowledge-proofs-for-better-patient-interactions-with-blockchain-technology.html, Accessed on Jun. 5, 2018.

Sanna et al., "e-Health," Digital Privacy, 2011, p. 697-720, Chapter 26, LNCS 6545, Springer-Verlag Berlin Heidelberg.

Yang et al., "A Smart-Card-Enabled Privacy Preserving E-Prescription System," IEEE Transactions on Information Technology in Biomedicine, Mar. 2004, p. 47-58, vol. 8, No. 1.

\* cited by examiner

ZERO KNOWLEDGE MULTI-PARTY PRESCRIPTION MANAGEMENT AND DRUG INTERACTION PREVENTION SYSTEM

BACKGROUND

Embodiments of the present invention relate generally to the field of computing and more particularly to data processing and data security using a combination of multi-party computation techniques.

Drug overdoses and adverse medical reactions due to multiple conflicting prescriptions, oftentimes from multiple healthcare providers, are just a few examples of unintended consequences of poor drug prescription management.

In today's day and age, privacy of one's health, medical conditions, and prescription drugs is a top concern for various individuals, especially those who may see multiple physicians for various problems. An individual may be prescribed an anti-depressant for their depression, a pain medication for their sports injury, a statin for their high cholesterol levels, and insulin for their diabetes. Multiple medications prescribed by multiple healthcare providers may cause repeat medications to be prescribed, as well as adverse drug interactions.

SUMMARY

Embodiments of the invention include a method, computer program product, and system, for implementing a secure system to prevent adverse drug interactions and repeat prescriptions, for a patient, in a multi-party computing environment.

A method, according to an embodiment of the invention, for implementing a secure system to prevent adverse drug interactions and repeat prescriptions, for a patient, in a multi-party computing environment, includes receiving, by a first computer, a patient identifier from a provider, wherein the patent identifier corresponds to a patient. The method further includes authenticating, by the first computer, an access by the provider and retrieving, by the first computer, a second patient identifier, wherein the second patient identifier corresponds to the received patient identifier, wherein the received patient identifier and the second patient identifier are different. The method further includes receiving, by the first computer, an input from the provider that corresponds to the patient identifier, and accessing, by the first computer, a secure database that contains a stored private ID, wherein the stored private ID is a combination of the received patient identifier and the retrieved second patient identifier, and wherein the secure database includes data relating to the patient. The method further includes searching, by the first computer, the secure database to obtain a search result based on the received input from the provider, and transmitting, by the first computer, the search result to the provider.

A computer program product, according to an embodiment of the invention, includes a non-transitory tangible storage device having program code embodied therewith. The program code is executable by a processor of a computer to perform a method. The method includes receiving, by a first computer, a patient identifier from a provider, wherein the patent identifier corresponds to a patient. The method further includes authenticating, by the first computer, an access by the provider and retrieving, by the first computer, a second patient identifier, wherein the second patient identifier corresponds to the received patient identifier, wherein the received patient identifier and the second patient identifier are different. The method further includes receiving, by the first computer, an input from the provider that corresponds to the patient identifier, and accessing, by the first computer, a secure database that contains a stored private ID, wherein the stored private ID is a combination of the received patient identifier and the retrieved second patient identifier, and wherein the secure database includes data relating to the patient. The method further includes searching, by the first computer, the secure database to obtain a search result based on the received input from the provider, and transmitting, by the first computer, the search result to the provider.

A computer system, according to an embodiment of the invention, includes one or more computer devices each having one or more processors and one or more tangible storage devices; and a program embodied on at least one of the one or more storage devices, the program having a plurality of program instructions for execution by the one or more processors. The program instructions implement a method. The method includes program instructions for receiving, by a first computer, a patient identifier from a provider, wherein the patent identifier corresponds to a patient. The method further includes authenticating, by the first computer, an access by the provider and retrieving, by the first computer, a second patient identifier, wherein the second patient identifier corresponds to the received patient identifier, wherein the received patient identifier and the second patient identifier are different. The method further includes receiving, by the first computer, an input from the provider that corresponds to the patient identifier, and accessing, by the first computer, a secure database that contains a stored private ID, wherein the stored private ID is a combination of the received patient identifier and the retrieved second patient identifier, and wherein the secure database includes data relating to the patient. The method further includes searching, by the first computer, the secure database to obtain a search result based on the received input from the provider, and transmitting, by the first computer, the search result to the provider.

DETAILED DESCRIPTION

Currently, drug prescription management databases that seek to reduce prescriptions that are repeats or have unintended adverse drug interactions with patients' existing prescriptions, or conditions, are addressed through proprietary provider specific systems which do not have any inherent privacy protection for users nor do they address the need for multiple providers to interact with a common system while providing privacy to the users.

The present invention discloses a system that allows for the aggregation of a patient's drug prescription data and medical condition data in a way that inherently preserves the patient's privacy, by using a combination of two cryptographic multi-party computation (MPC) techniques: Oblivious pseudo random function (OPRF) and private set intersection (PSI). This unique combination not only enables privacy for individual patients, but the combination of OPRF and PSI allows the queries from one or more healthcare providers to be performed privately too.

Hereinafter, exemplary embodiments of the present invention will be described in detail with reference to the attached drawings.

The present invention is not limited to the exemplary embodiments below, but may be implemented with various modifications within the scope of the present invention. In addition, the drawings used herein are for purposes of illustration, and may not show actual dimensions.

Figure 1:
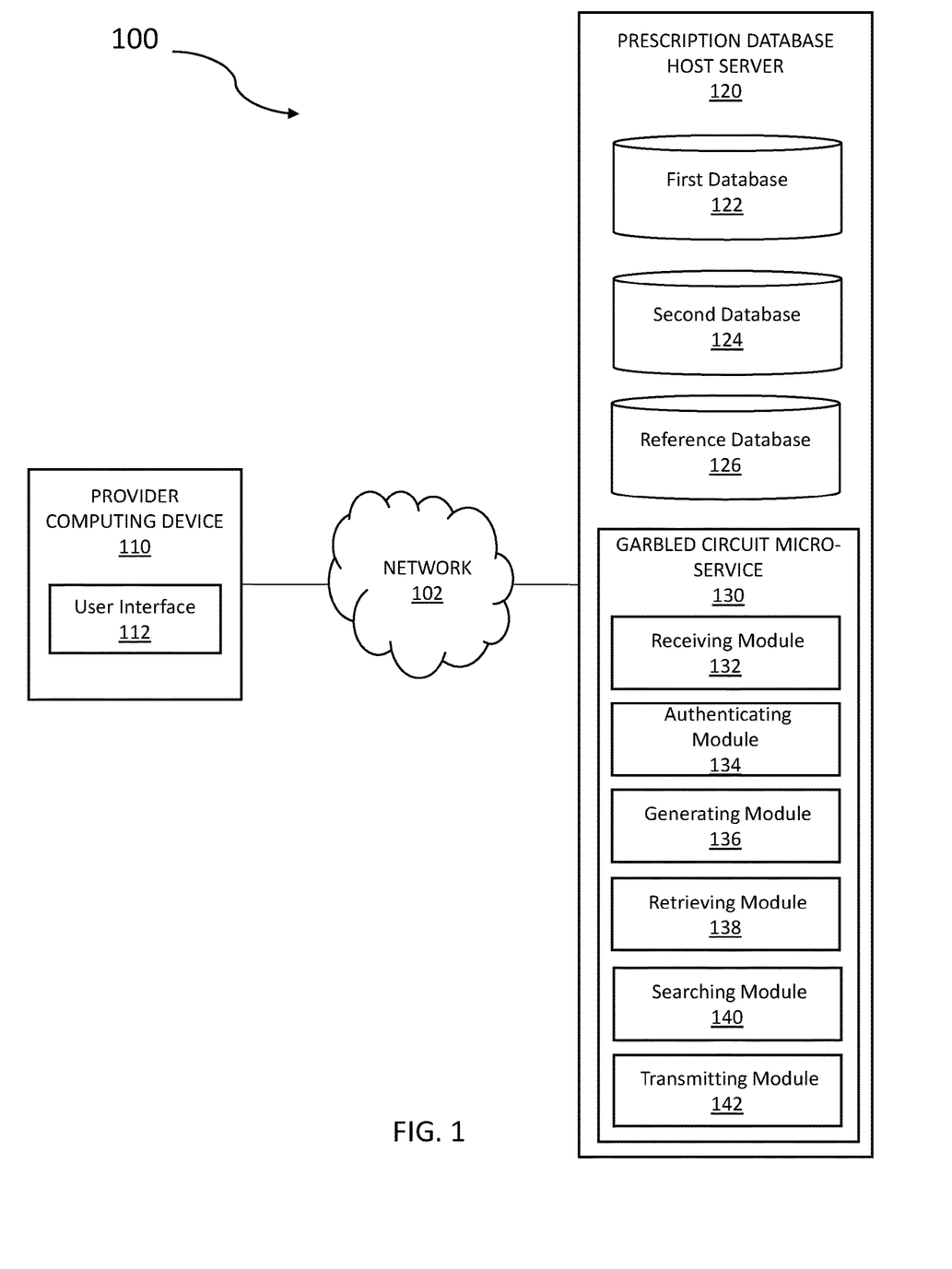
FIG. 1 illustrates a multi-party computing environment, in accordance with an embodiment of the present invention.

FIG. 1 illustrates multi-party computing environment 100, in accordance with an embodiment of the present invention. Multi-party computing environment 100 includes provider computing device 110 and prescription database host server 120 connected via network 102. The setup in FIG. 1 represents an example embodiment configuration for the present invention, and is not limited to the depicted setup in order to derive benefit from the present invention.

In an exemplary embodiment, provider computing device 110 contains user interface 112. In various embodiments, provider computing device 110 may be a laptop computer, tablet computer, netbook computer, personal computer (PC), a desktop computer, a personal digital assistant (PDA), a smart phone, or any programmable electronic device capable of communicating with prescription database host server 120 via network 102. Provider computing device 110 may include internal and external hardware components, as depicted and described in further detail below with reference to FIG. 4. In other embodiments, provider computing device 110 may be implemented in a cloud computing environment, as described in relation to FIGS. 5 and 6, herein. Provider computing device 110 may also have wireless connectivity capabilities allowing it to communicate with prescription database host server 120, as well as other computers or servers over network 102.

In an exemplary embodiment, user interface 112 may be a computer program that allows a healthcare provider (e.g., doctor, pharmacist, nurse, or any other medical professional) to interact with provider computing device 110 and other connected devices via network 102. For example, user interface 112 may be a graphical user interface (GUI). In addition to comprising a computer program, user interface 112 may be connectively coupled to hardware components, such as those depicted in FIG. 4, for receiving user input. In an exemplary embodiment, user interface 112 is a web browser, however in other embodiments user interface 112 may be a different program capable of receiving user interaction and communicating with other devices.

In exemplary embodiments, prescription database host server 120 contains first database 122, second database 124, reference database 126, and garbled circuit micro-service 130. In various embodiments, prescription database host server 120 may be a laptop computer, tablet computer, netbook computer, personal computer (PC), a desktop computer, a personal digital assistant (PDA), a smart phone, a server, or any programmable electronic device capable of communicating with provider computing device 110 via network 102. Prescription database host server 120 may include internal and external hardware components, as depicted and described in further detail below with reference to FIG. 4.

While prescription database host server 120 is shown as a single device, in other embodiments, prescription database host server 120 may be comprised of a cluster or plurality of computing devices, working together or working separately. In other embodiments, prescription database host server 120 may be implemented in a cloud computing environment, as described in relation to FIGS. 5 and 6, herein. Prescription database host server 120 may also have wireless connectivity capabilities allowing it to communicate with provider computing device 110, as well as other computers or servers over network 102.

With continued reference to FIG. 1, first database 122 contains a patient identifier, as provided by the patient's healthcare provider, and a unique second patient identifier that is assigned to the patient identifier by generating module 136. In exemplary embodiments, a patient identifier may be a unique combination of identifying numbers and letters, a social security number, or any other identifying code, or sequence, that is associated with a particular patient. In exemplary embodiments, the unique second patient identifier may be a pseudo-randomly generated, via generating module 136, string of characters, numbers, and symbols that is paired with the patient identifier. As will be discussed in further detail below, the assigned second patient identifier that is generated is only known to the prescription database host server 120, and is not revealed to the healthcare provider or patient. Furthermore, a private ID is generated as a product of the combination of the patient identifier and the assigned second patient identifier.

In exemplary embodiments, first database 122 stores the generated private ID, which is a combination of the patient identifier (as provided by the healthcare provider) with its corresponding assigned second patient identifier (as provided by prescription database host server's 120 assigned private key) as a dataset. For example, a dataset in first database 122 may appear as <GeneratedPrivateID=SSN, AssignedPrivateKey>.

In exemplary embodiments, oblivious pseudo random function (OPRF) is the multi-party computation technique used to generate the private ID. OPRF thus enables two parties (e.g., healthcare provider 110 and prescription database host server 120) with secret inputs to interactively compute a pseudo-random string, similar to a hash, without either party revealing their input to the other.

With continued reference to FIG. 1, second database 124 stores information corresponding to the generated private ID for a patient. Examples of stored information on second database 124 may include drug prescriptions, medical history, adverse drug interactions, known allergies, medical conditions that may influence whether a certain drug is prescribed to the patient, and so forth. In exemplary embodiments, the information stored on second database 124 is private and not revealed, in its totality, to either the healthcare provider, the database host, the patient, or to any other party. For example, second database 124 may store multiple drug prescriptions for a particular patient (each private ID) from multiple healthcare providers in this central location database.

In exemplary embodiments, second database 124 is independent of first database 122 and does not communicate with first database 122. The information stored on second database 124 is only relatable to a particular patient by an autonomous private ID, which is generated via a separate multi-party computation (as discussed above) and stored in first database 122. In all other respects, the private drug prescription information and medical history, associated with the generated private ID, on second database 124 is strictly confidential. The information on second database 124 may be stored as datasets, or as arrays. For example, a dataset in second database 124 may appear as <GeneratedPrivateID, drugCode1>; <GeneratedPrivateID, drugCode2>; <GeneratedPrivateID, medicalCondition1>; <GeneratedPrivateID, medicalCondition2> and so forth. An array in second database 124 may appear as a table that is pre-populated with drug prescriptions for a patient (i.e., as identified by their respective private ID), existing medical conditions of a patient, prior medical history of a patient, and any other relevant medical information that may influence a proposed new drug prescription for a patient, by a healthcare provider.

In exemplary embodiments, private set intersection (PSI) is the multi-party computation technique used to allow the two parties (e.g., provider computing device 110 and prescription database host server 120) with secret inputs to interactively compute the intersection of two sets of data (e.g., the proposed drug prescription information for a patient and the current drug prescription information for a patient), without revealing the full sets to each other. For example, if a healthcare provider needs to prescribe a certain medication to a patient, the present invention is capable of returning a collision value, only, to the healthcare provider, advising that the patient already has a current prescription for the proposed drug (perhaps prescribed by another healthcare provider), without revealing any other private information about the patient.

With continued reference to FIG. 1, reference database 126 may include stored medical information, such as adverse drug interactions between prescription drugs, drugs to avoid for patients with various medical conditions, and additional encyclopedic medical information. In exemplary embodiments, the information stored in reference database 126 may be organized as an array where a variable, such as a proposed prescription drug for a patient (e.g., <NewDrugCode>) may be indexed to determine if the new proposed prescription drug has any adverse drug interactions with existing drug prescriptions of a patient, or with any existing medical conditions of a patient.

With continued reference to FIG. 1, garbled circuit micro-service 130 contains instruction sets, executable by a processor, which may be described using a set of functional modules. The functional modules of garbled circuit micro-service 130 include receiving module 132, authenticating module 134, generating module 136, retrieving module 138, searching module 140, and transmitting module 142. In an exemplary embodiment, garbled circuit micro-service 130 is depicted as a separate program on prescription database host server 120. In alternative embodiments, garbled circuit micro-service 130 may be a stand-alone program, or contained as a separate program on another server connected to prescription database host server 120, via network 102.

A garbled circuit is a cryptographic protocol that enables two-party secure computation in which two mistrusting parties can jointly evaluate a function over their private inputs without the presence of a trusted third party.

A micro-service is a software development technique, a variant of the service oriented architecture (SOA) style that structures an application as a collection of loosely coupled services. In a micro-service architecture, services are fine-grained and the protocols are lightweight. The benefit of decomposing an application into different smaller services is that it improves modularity and makes the application easier to understand, develop, test, and more resilient to architecture erosion. Micro-service based architectures enable continuous delivery and deployment.

Figure 2:
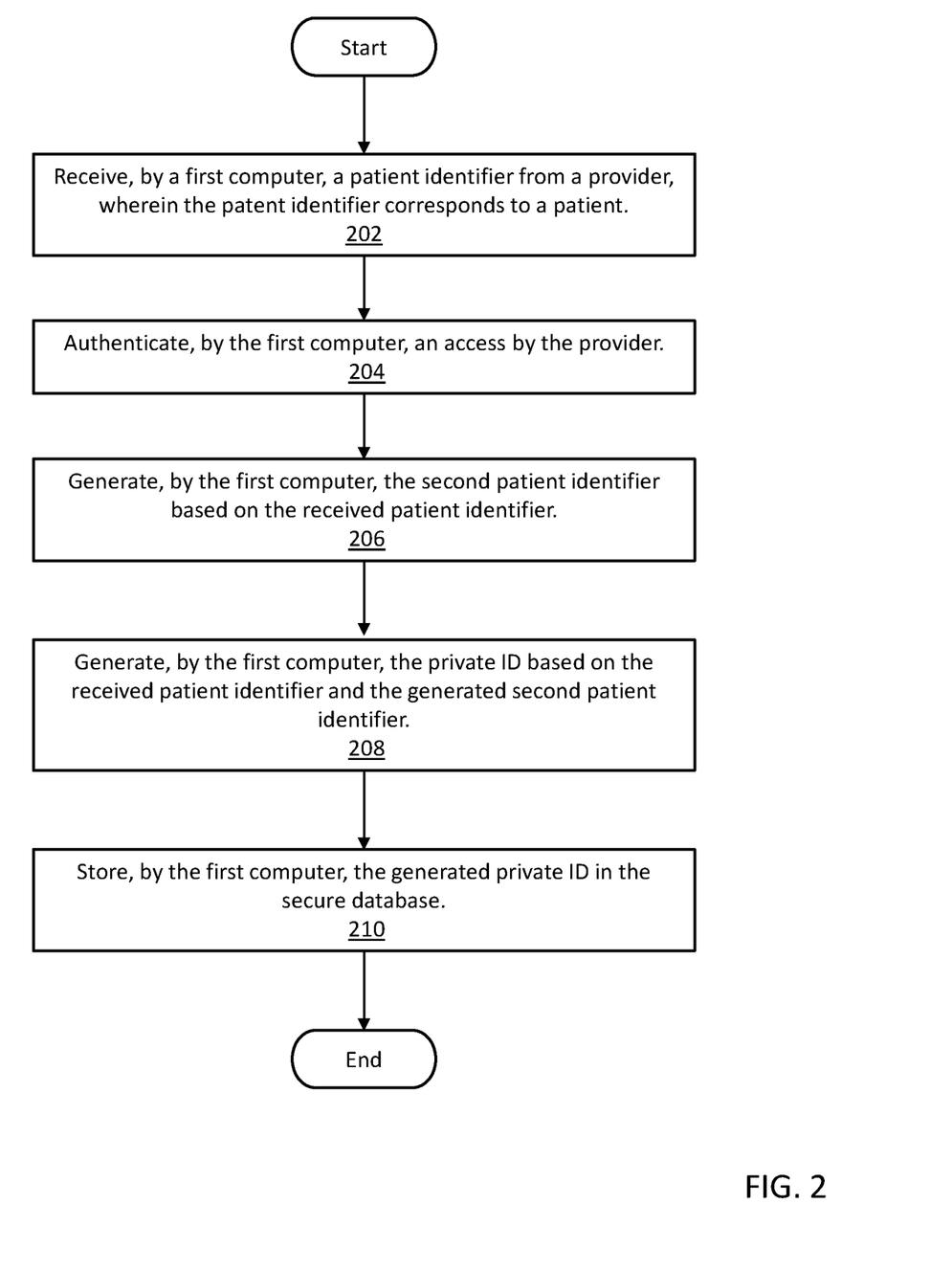
FIG. 2 is a flowchart illustrating the operation of generating a second patient identifier and a private identification (ID), based on a received patient identifier, in accordance with an embodiment of the present invention.

FIG. 2 is a flowchart illustrating the operation of generating a second patient identifier and a private ID, based on a received patient identifier, in accordance with an embodiment of the present invention.

With reference to FIGS. 1 and 2, receiving module 132 includes a set of programming instructions in garbled circuit micro-service 130. The set of programming instructions is executable by a processor. Receiving module 132 receives, by a first computer (i.e., prescription database host server 120), a patient identifier from a provider (i.e., provider computing device 110), wherein the patient identifier corresponds to a patient (step 202).

With reference to an illustrative example, Dr. Pepper needs to prescribe a blood-thinning medication to his patient, Lewis. Dr. Pepper must first create a database holder for Lewis, since this is Lewis' first time to his office. As such, Dr. Pepper creates a unique identifying string of numbers, Lewis' social security number, to enter into his provider computing device 110. Receiving module 132, of prescription database host server 120, receives the social security number.

With continued reference to FIGS. 1 and 2, authenticating module 134 includes a set of programming instructions in garbled circuit micro-service 130. The set of programming instructions is executable by a processor. Authenticating module 134 authenticates, by the first computer (i.e., prescription database host server 120), an access by the provider (step 204).

In exemplary embodiments, authenticating module 134 authenticates a healthcare provider (e.g., doctor, pharmacist, nurse practitioner, etc.) by means of a username, or identification number, and associated physician ID or government issued ID string that matches the healthcare provider's username or identification number. This security features ensures that only legally registered healthcare providers are permitted to prescribe drugs for a patient, and access the prescription database host server 120.

With continued reference to the illustrative example, Dr. Pepper must be authenticated prior to accessing the prescription database host server 120. As such, Dr. Pepper is required to enter a username and password, a government issued ID and access code, a healthcare provider licensing number, or any other such combination of private identifiers known to one of ordinary skill in the art that provides a level of trust between the healthcare provider and access to information potentially concerning Lewis' private medical history, current prescriptions, and potential adverse reactions.

In exemplary embodiments, secure measures may be in place to protect the security of second database 124. For example, authenticating module 134 may authenticate access for healthcare providers with limits as to how many queries they can make per patient, and allow healthcare providers to store drug prescriptions and standard-coded medical conditions per patient. Furthermore, pharmacists may be able to store times/dates when prescriptions are filled, quantity of the drug, whether it is a re-fill, an expiration date, and so forth.

With further reference to FIGS. 1 and 2, generating module 136 includes a set of programming instructions in garbled circuit micro-service 130. The set of programming instructions is executable by a processor. Generating module 136 generates, by the first computer (i.e., prescription database host server 120), a second patient identifier based on the received patient identifier (step 206). In exemplary embodiments, the second patient identifier is a randomly assigned private key (e.g., a combination of characters, numbers, and symbols) that corresponds to the received patient identifier (e.g., social security number).

With continued reference to FIGS. 1 and 2, generating module 136 further generates, by the first computer (i.e., prescription database host server 120), a private ID based on the received patient identifier and the generated second patient identifier (step 208). In exemplary embodiments, generating module 136 generates the private ID through a multi-party computation technique known as oblivious pseudo-random function (OPRF).

OPRF enables two parties with secret inputs to interactively compute a pseudo-random string similar to a hash, but without either party revealing their input to the other. As such, the generated private ID is derived through the OPRF function from the combination of the healthcare provider's patient identifier (e.g., social security number) and the prescription database host's randomly assigned private key.

In exemplary embodiments, generating module 136 stores, by the first computer (i.e., prescription database host server 120), the generated private ID in a secure database, such as first database 122 (step 210).

With continued reference to the illustrative example above, once Dr. Pepper has been authenticated to access the prescription database host server 120 and has provided Lewis' patient identifier (e.g., social security number), generating module 136 provides a randomly assigned string, only known to prescription database host server 120, to be paired with Lewis' social security number. Once a patient's identifier is paired with the host database's private string, generating module 136 generates a private ID to be stored in first database 122 on prescription database host server 120. In exemplary embodiments, the generation of a private ID is done only once at setup. Thereafter, Dr. Pepper, and any other of Lewis' healthcare providers (once authenticated) may access the prescription database host server 120 and perform autonomous queries, or searches, for overlaps/contraindications of Lewis' prescriptions. In response to the search, the healthcare provider may receive a set of possible yes/no, NULL, or collision value results.

Figure 3:
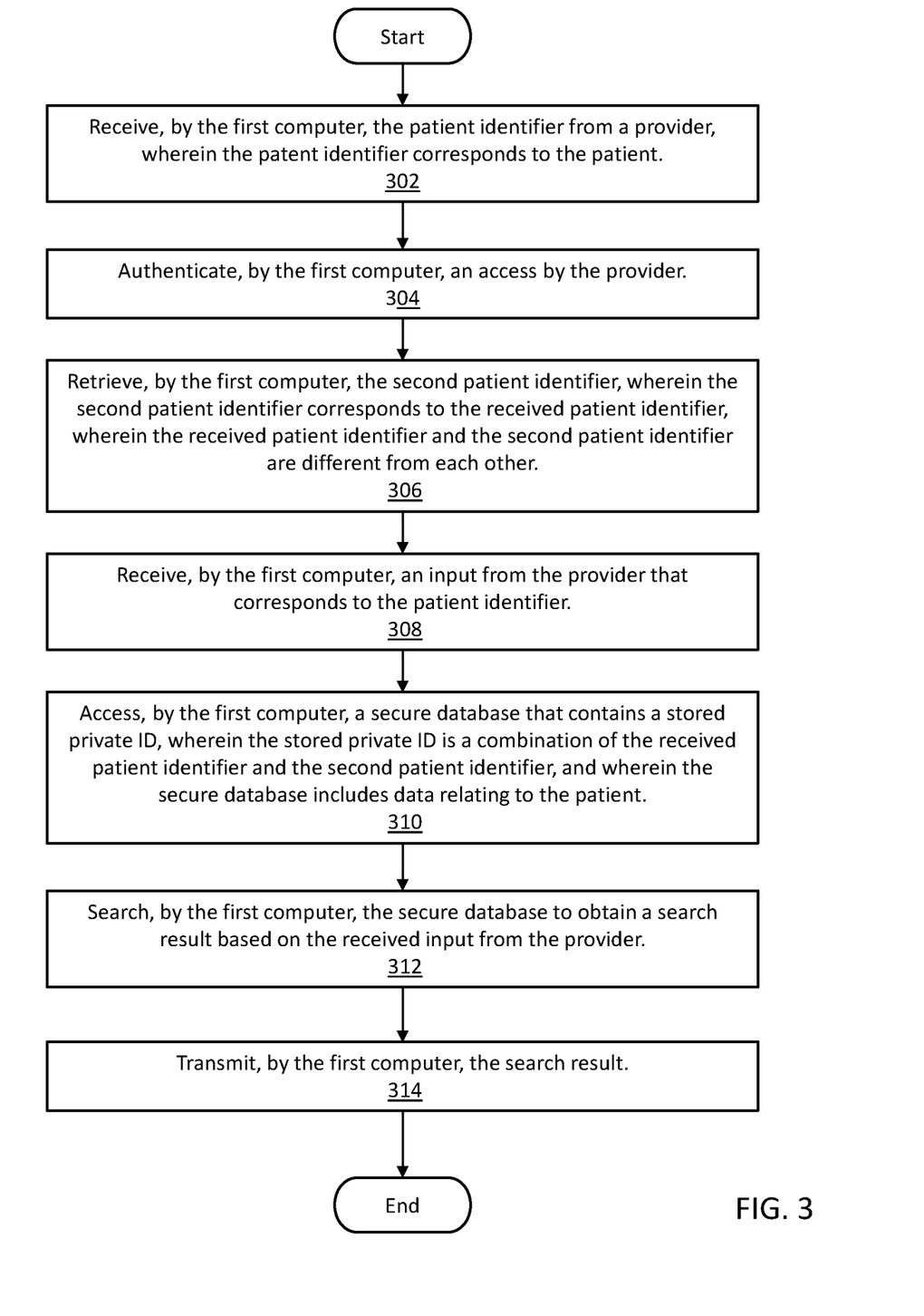
FIG. 3 is a flowchart illustrating the operation of garbled circuit micro-service, in accordance with an embodiment of the present invention.

FIG. 3 is a flowchart illustrating the operation of garbled circuit micro-service 130, in accordance with an embodiment of the present invention.

With reference to FIGS. 1 and 3, receiving module 132 includes a set of programming instructions in garbled circuit micro-service 130. The set of programming instructions is executable by a processor. Receiving module 132 receives, by a first computer, a patient identifier from a provider, wherein the patent identifier corresponds to a patient (step 302).

With continued reference to FIGS. 1 and 3, authenticating module 134 includes a set of programming instructions in garbled circuit micro-service 130. The set of programming instructions is executable by a processor. Authenticating module 134 authenticates, by the first computer, an access by the provider (step 304).

With continued reference to FIGS. 1 and 3, retrieving module 138 includes a set of programming instructions in garbled circuit micro-service 130. The set of programming instructions is executable by a processor. Retrieving module 138 retrieves, by the first computer (i.e., prescription database host server 120) a second patient identifier, wherein the second patient identifier corresponds to the received patient identifier, wherein the received patient identifier and the second patient identifier are different (step 306). In exemplary embodiments, retrieving module 138 may only be capable of retrieving the second patient identifier after generating module 136 has already generated and assigned a second patient identifier to the received patient identifier (see step 206). As discussed above, the paired patient identifier and second patient identifier dataset combine to produce a private ID, which is then stored in first database 122.

With continued reference to FIGS. 1 and 3, receiving module 132 receives, by the first computer (i.e., prescription database host server 120), an input from the provider (i.e., provider computing device 110) that corresponds to the patient identifier (step 308). In exemplary embodiments, an input may be a proposed drug prescription for the patient, a search query regarding a patient's drug history, a patient's medical conditions, and so forth.

With continued reference to FIGS. 1 and 3, searching module 140 includes a set of programming instructions in garbled circuit micro-service 130. The set of programming instructions is executable by a processor. Searching module 140 accesses, by the first computer (i.e., prescription database host server 120), a secure database that contains a stored private ID, wherein the stored private ID is a combination of the received patient identifier and the retrieved second patient identifier, and wherein the secure database (e.g., such as second database 124) includes data relating to the patient (step 310). In exemplary embodiments, the data relating to the patient may include drug prescriptions, medical conditions, previous medical procedures, and so forth. The private ID stored in first database 122 is used by searching module 140 to search a patient's private medical information in second database 124.

With continued reference to FIGS. 1 and 3, searching module 140 searches the secure database (e.g., second database 124) to obtain a search result based on the received input from the provider (step 312). In various embodiments, the healthcare provider may need to identify whether a proposed drug prescription has previously, or is currently, prescribed to a patient. In other embodiments, the healthcare provider may need to identify whether a proposed drug prescription will have any adverse reactions, or contraindications, with other drugs or medical conditions that a patient currently has, or is taking.

In exemplary embodiments, searching module 140 may be capable of identifying a duplication of the received input from the provider that corresponds to the private ID in the secure database (e.g., second database 124).

With reference to the illustrative example above, searching module 140 may reveal that the prospective drug prescription that Dr. Pepper was going to prescribe has been previously prescribed and is one of Lewis' active prescriptions. Based on this information, Dr. Pepper knows not to duplicate this prescription and may instead opt to see how Lewis' health improves over time with the active prescription.

In further embodiments, searching module 140 may be capable of identifying a contraindication of the received input, from the provider, with one or more inputs that correspond to the private ID in the secure database (e.g., second database 124).

In exemplary embodiments, searching module 140 may identify a contraindication of the received input, from the provider, with one or more inputs that correspond to the private ID by consulting a reference database (e.g., reference database 126) that comprises a pre-populated table of contraindications for one or more drugs relating to the received input from the provider.

With continued reference to the illustrative example above, searching module 140 may reveal that the prospective drug prescription, and dosage, that Dr. Pepper was going to prescribe adversely interacts with another drug that Lewis is currently taking. However, Dr. Pepper knows that a lower dosage, of the prospective drug prescription, does not have any contraindications with other drugs that Lewis is currently taking, and therefore moves ahead with prescribing the lower dosage of the prospective drug.

In exemplary embodiments, searching module 140 identifies a duplication of the received input, from the provider, that corresponds to the private ID in the secure database, and identifies a contraindication of the received input, from the provider, with one or more inputs that correspond to the private ID in the secure database, through a multi-party computation technique known as private set intersection (PSI).

PSI allows two parties with secret inputs, or sets of items, to interactively compute the intersection of the two sets, without revealing the full sets to each other. As such, PSI based service allows an authenticated healthcare provider to see if a patient already has a prescription. The healthcare provider does not learn of any other prescriptions of a patient, and the prescription database host server 120 does not learn what the healthcare provider is searching for.

In alternative embodiments, all that may be required is for a single entry, or input, from the healthcare provider to be searched in second database 124, which may be accomplished in the form of a simpler garbled circuit multi-party computation operation.

With reference to the illustrative example, Dr. Pepper tries to enter a pain medication for Lewis into prescription database host server 120. Searching module 140 utilizes PSI to identify whether the proposed pain medication is already prescribed to Lewis in second database 124. If the pain medication is already prescribed to Lewis, then searching module 140 will identify this and report a collision value to Dr. Pepper.

In exemplary embodiments, prescription database host server 120 maintains a mapping of potential interactions per drug prescription for each private ID (i.e., anonymous patient). This enables a healthcare provider to query a new drug prescription against the full set of potential interactions with various drugs and medical conditions of a particular patient, using PSI. In a basic embodiment, the healthcare provider receives a yes/no value, with regards to a new drug prescription having an interaction with various other drugs and medical conditions of a patient, and is not told the specific drug interaction. Furthermore, the prescription database host server 120 does not learn what the prospective drug prescription is for the associated private ID.

In alternative embodiments, the drug and medical condition interaction may be split into two tests per private ID. The first test may be interactions with drugs and medical conditions entered by the same healthcare provider. The second test may be interactions with drugs and medical conditions entered by other healthcare providers, of which the current healthcare provider is not necessarily aware of.

In further alternative embodiments, second database 124 may be used by governmental agencies, such as the Food and Drug Administration (FDA), pharmaceutical companies, and perhaps even medical malpractice trial lawyers, to determine if information that was presented either in clinical trials, medical testimony, and so forth for a drug is equivalent to the actual results. Based on actual findings, corrections may be made regarding accurately reported side effects.

As discussed above, a preferred embodiment keeps the OPRF system of first database 122 separate from the PSI database query system of second database 124.

With continued reference to FIGS. 1 and 3, transmitting module 142 includes a set of programming instructions in garbled circuit micro-service 130. The set of programming instructions is executable by a processor. Transmitting module 142 transmits, by the first computer (i.e., prescription database host server 120), the search result to the provider (step 314).

In exemplary embodiments, transmitting module 142 transmits a collision value to the provider, in response to identifying a duplication of the received input, from the provider, that corresponds to the private ID in the secure database (i.e., second database 124).

With reference to the illustrative example above, since the pain medication that Dr. Pepper was proposing to prescribe to Lewis has been identified as already being prescribed to Lewis, transmitting module 142 sends a message to Dr. Pepper (i.e., provider computing device 110), via network 102, with a collision value.

In exemplary embodiments, transmitting module 142 transmits a "yes" value to the provider, in response to identifying a contraindication of the received input, from the provider, with one or more inputs that correspond to the private ID in the secure database.

In various alternative embodiments, a drug interaction list may be transmitted, via transmitting module 142, directly to the patient's electronic device while the healthcare provider is only informed that the search query returned a non-NULL value thereby indicating that there is at least one possible adverse drug interaction between the proposed drug prescription and other drugs, or medical conditions, related to the patient. The patient, thus, maintains optimal privacy and has the option to reveal the full drug interaction list to their healthcare provider at their discretion.

With reference to the illustrative example above, Dr. Pepper decides to propose a less potent pain medication to Lewis based on the collision value received for the original proposed prescription. This time, searching module 140 identifies a contraindication with one or more other prescriptions that Lewis is currently on. As such, transmitting module 142 sends a message to Dr. Pepper (i.e., provider computing device 110), via network 102, with a "yes" value indicating that adverse drug interactions may occur if the proposed prescription is entered. However, transmitting module 142 does not transmit the names of any other medications, nor the potential adverse reactions, or drug interactions, that may occur, thereby maintaining Lewis' privacy.

In exemplary embodiments, transmitting module 142 may transmit a NULL value to the provider, in response to not identifying a duplication of the received input from the provider that corresponds to the private ID in the secure database, and in response to not identifying a contraindication of the received input, from the provider, with one or more inputs that correspond to the private ID in the secure database. Furthermore, transmitting module 142 may be capable of updating the secure database (e.g., second database 124) to include the received input from the provider that corresponds to the private ID.

With reference to the illustrative example above, if the proposed pain medication to be prescribed to Lewis, by Dr. Pepper, is not currently prescribed to Lewis nor causes any adverse interactions with other drugs that Lewis may be taking, according to searching module 140's results, transmitting module 142 updates Lewis's private ID in second database 124 to include the pain medication prescribed by Dr. Pepper.

In an exemplary embodiment, network 102 is a communication channel capable of transferring data between connected devices and may be a telecommunications network used to facilitate telephone calls between two or more parties comprising a landline network, a wireless network, a closed network, a satellite network, or any combination thereof. In another embodiment, network 102 may be the Internet, representing a worldwide collection of networks and gateways to support communications between devices connected to the Internet. In this other embodiment, network 102 may include, for example, wired, wireless, or fiber optic connections which may be implemented as an intranet network, a local area network (LAN), a wide area network (WAN), or any combination thereof. In further embodiments, network 102 may be a Bluetooth network, a WiFi network, or a combination thereof. In general, network 102 can be any combination of connections and protocols that will support communications between provider computing device 110 and prescription database host server 120.

Figure 4:
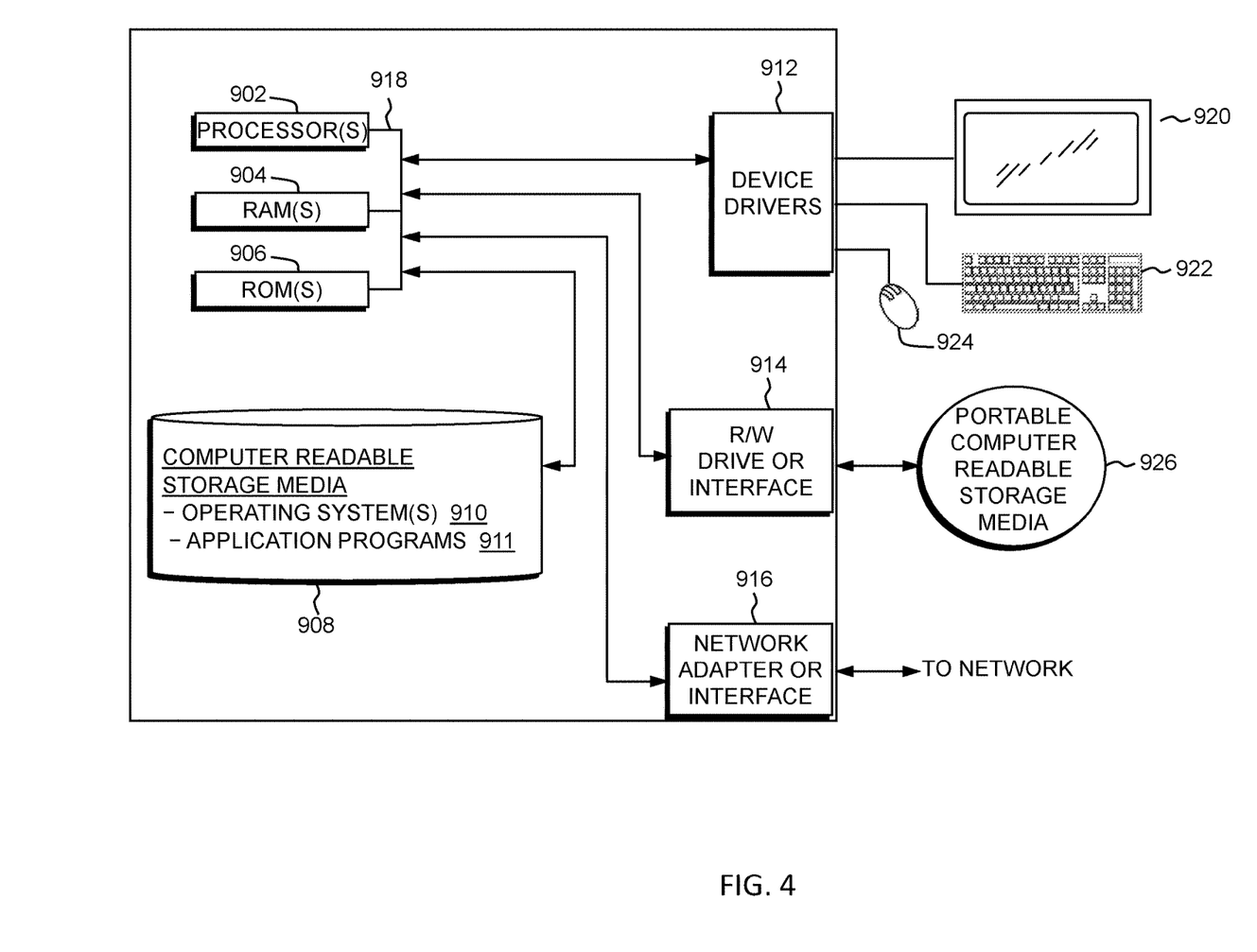
FIG. 4 depicts the hardware components of the multi-party computing environment of FIG. 1, in accordance with an embodiment of the present invention.

FIG. 4 is a block diagram depicting components of a computing device in accordance with an embodiment of the present invention. It should be appreciated that FIG. 4 provides only an illustration of one implementation and does not imply any limitations with regard to the environments in which different embodiments may be implemented. Many modifications to the depicted environment may be made.

Computing device of FIG. 4 may include one or more processors 902, one or more computer-readable RAMs 904, one or more computer-readable ROMs 906, one or more computer readable storage media 908, device drivers 912, read/write drive or interface 914, network adapter or interface 916, all interconnected over a communications fabric 918. Communications fabric 918 may be implemented with any architecture designed for passing data and/or control information between processors (such as microprocessors, communications and network processors, etc.), system memory, peripheral devices, and any other hardware components within a system.

One or more operating systems 910, and one or more application programs 911 may be stored on one or more of the computer readable storage media 908 for execution by one or more of the processors 902 via one or more of the respective RAMs 904 (which typically include cache memory). In the illustrated embodiment, each of the computer readable storage media 908 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Computing device of FIG. 4 may also include a R/W drive or interface 914 to read from and write to one or more portable computer readable storage media 926. Application programs 911 on computing device may be stored on one or more of the portable computer readable storage media 926, read via the respective R/W drive or interface 914 and loaded into the respective computer readable storage media 908.

Computing device of FIG. 4 may also include a network adapter or interface 916, such as a TCP/IP adapter card or wireless communication adapter (such as a 4G wireless communication adapter using OFDMA technology). Application programs 911 on computing device of FIG. 4 may be downloaded to the computing device from an external computer or external storage device via a network (for example, the Internet, a local area network or other wide area network or wireless network) and network adapter or interface 916. From the network adapter or interface 916, the programs may be loaded onto computer readable storage media 908. The network may comprise copper wires, optical fibers, wireless transmission, routers, firewalls, switches, gateway computers and/or edge servers.

Computing device of FIG. 4 may also include a display screen 920, a keyboard or keypad 922, and a computer mouse or touchpad 924. Device drivers 912 interface to display screen 920 for imaging, to keyboard or keypad 922, to computer mouse or touchpad 924, and/or to display screen 920 for pressure sensing of alphanumeric character entry and user selections. The device drivers 912, R/W drive or interface 914 and network adapter or interface 916 may comprise hardware and software (stored on computer readable storage media 908 and/or ROM 906).

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
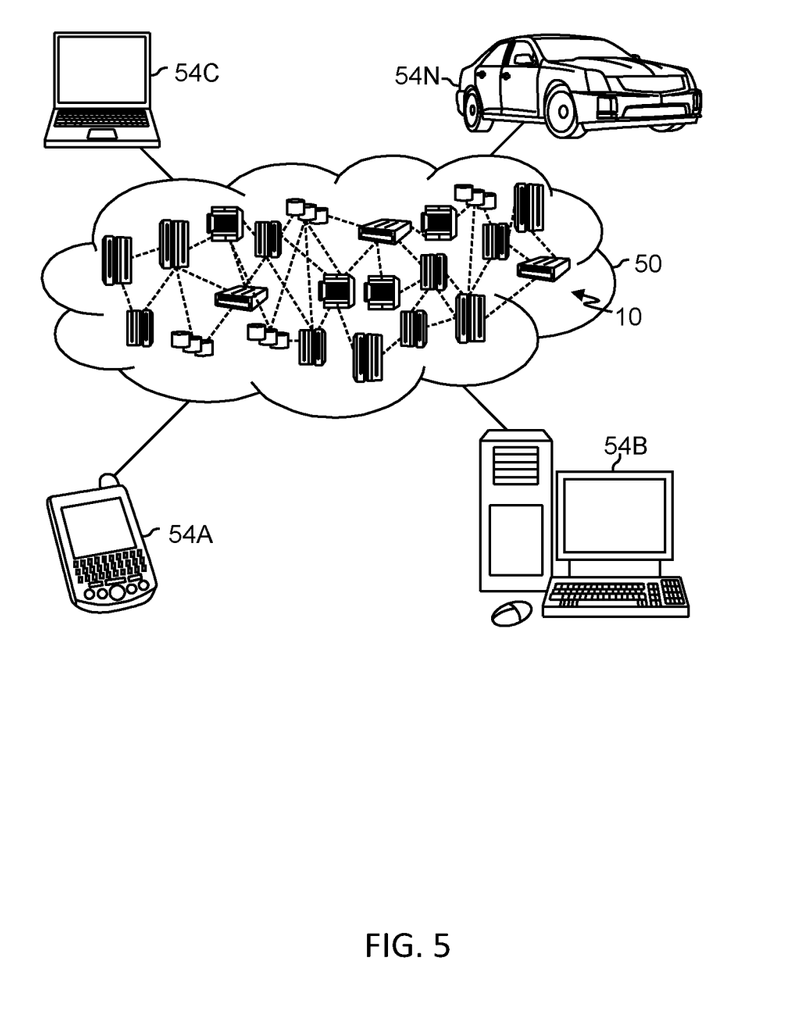
FIG. 5 depicts a cloud computing environment, in accordance with an embodiment of the present invention.

Referring now to FIG. 5, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
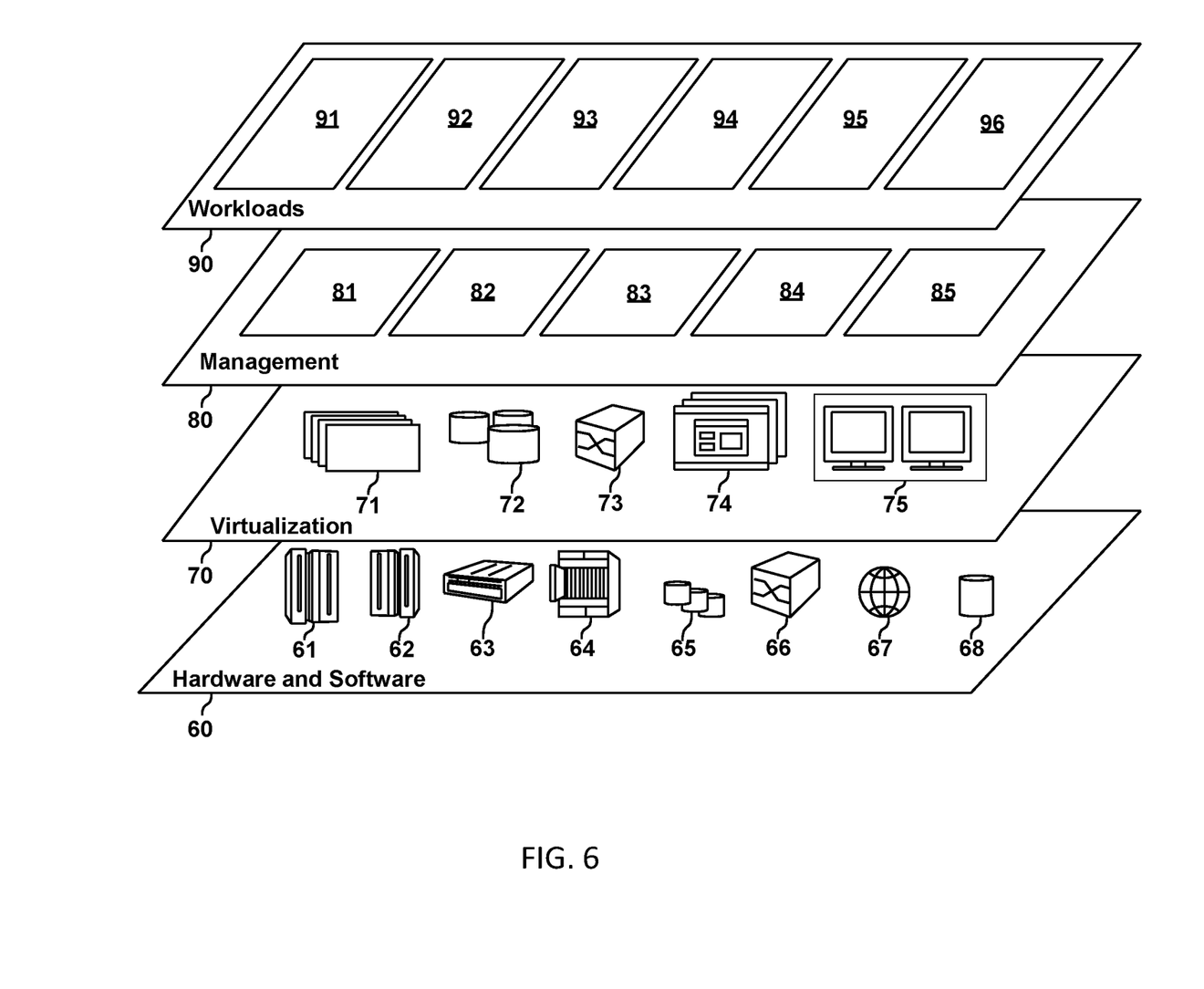
FIG. 6 depicts abstraction model layers of the illustrative cloud computing environment of FIG. 5, in accordance with an embodiment of the present invention.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; analytics services 96, including those described in connection with FIGS. 1-6.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for preserving data of a patient using a cryptographic multi-party computation (MPC), the method comprising:

receiving, by a first computer, a patient identifier from a provider, wherein the patient identifier corresponds to the patient, and wherein the first computer has a first database having an oblivious pseudo-random function (OPRF) system and a secured database having a separate private set intersection (PSI) query system, wherein the first database contains the patient identifier and a private identifier (ID), and wherein the secured database is private and stores information corresponding to the private ID;

authenticating, by the first computer, an access by the provider;

generating, by the first computer, a second patient identifier based on the received patient identifier;

generating, by the first computer, the private identifier (ID) based on the received patient identifier and the generated second patient identifier by using an OPRF of the OPRF system;

storing, by the first computer, the generated private ID in the first database;

retrieving, by the first computer, the second patient identifier, wherein the second patient identifier corresponds to the received patient identifier, wherein the received patient identifier and the second patient identifier are different;

receiving, by the first computer, an input from the provider that corresponds to the received patient identifier;

accessing, by the first computer, the secure database that contains the stored private identifier (ID), wherein the stored private ID is a combination of the received patient identifier and the retrieved second patient identifier, and wherein the secure database includes data relating to the patient;

searching, by the first computer, the secure database to obtain a search result based on the received input from the provider, by using a PSI function of the PSI system, wherein the PSI function is a cryptographic protocol that enables a two-party secure computation to obtain the search result from the secure database without a presence of a trusted third party and without revealing other information in the secure database corresponding to the private ID; and transmitting, by the first computer, the search result to the provider.

2. The method of claim 1, wherein searching, by the first computer, the secure database to obtain the search result based on the received input from the provider further comprises at least one of the following:

identifying a duplication of the received input from the provider that corresponds to the private ID in the secure database; and identifying a contraindication of the received input, from the provider, with one or more inputs that correspond to the private ID in the secure database, wherein the one or more inputs that correspond to the private ID in the secure database correspond to one or more medications that are already associated with the patient.

3. The method of claim 2, wherein identifying the contraindication of the received input, from the provider, with one or more inputs that correspond to the private ID, further comprises:

consulting a reference database that comprises a pre-populated table of contraindications for one or more drugs relating to the received input from the provider.

4. The method of claim 1, wherein transmitting, by the first computer, the search result, further comprises at least one of the following:

in response to identifying a duplication of the received input, from the provider, that corresponds to the private ID in the secure database, returning a collision value to the provider; and in response to identifying a contraindication of the received input, from the provider, with one or more inputs that correspond to the private ID in the secure database, returning a yes value to the provider.

5. The method of claim 1, further comprising:

in response to not identifying a duplication of the received input from the provider that corresponds to the private ID in the secure database and in response to not identifying a contraindication of the received input, from the provider, with one or more inputs that correspond to the private ID in the secure database, updating, by the first computer, the secure database to include the received input from the provider that corresponds to the private ID.

6. The method of claim 1, further comprising:

managing one or more medications associated with the patient, by one or more providers, using the MPC.

7. A computer program product for preserving data of a patient using a cryptographic multi-party computation (MPC), the computer program product comprising a non-transitory tangible storage device having program code embodied therewith, the program code executable by a processor of a computer to perform a method, the method comprising:

receiving, by a first computer, a patient identifier from a provider, wherein the patient identifier corresponds to the patient, and wherein the first computer has a first database having an oblivious pseudo-random function (OPRF) system and a secured database having a separate private set intersection (PSI) query system, wherein the first database contains the patient identifier and a private identifier (ID), and wherein the secured database is private and stores information corresponding to the private ID;

authenticating, by the first computer, an access by the provider;

generating, by the first computer, a second patient identifier based on the received patient identifier;

generating, by the first computer, the private identifier (ID) based on the received patient identifier and the generated second patient identifier by using an OPRF of the OPRF system;

storing, by the first computer, the generated private ID in the first database;

retrieving, by the first computer, the second patient identifier, wherein the second patient identifier corresponds to the received patient identifier, wherein the received patient identifier and the second patient identifier are different;

receiving, by the first computer, an input from the provider that corresponds to the received patient identifier;

accessing, by the first computer, the secure database that contains the stored private identifier (ID), wherein the stored private ID is a combination of the received patient identifier and the retrieved second patient identifier, and wherein the secure database includes data relating to the patient;

searching, by the first computer, the secure database to obtain a search result based on the received input from the provider, by using a PSI function of the PSI system, wherein the PSI function is a cryptographic protocol that enables a two-party secure computation to obtain the search result from the secure database without a presence of a trusted third party and without revealing other information in the secure database corresponding to the private ID; and transmitting, by the first computer, the search result to the provider.

8. The computer program product of claim 7, wherein searching, by the first computer, the secure database to obtain the search result based on the received input from the provider further comprises at least one of the following:
 identifying a duplication of the received input from the provider that corresponds to the private ID in the secure database; and
 identifying a contraindication of the received input, from the provider, with one or more inputs that correspond to the private ID in the secure database, wherein the one or more inputs that correspond to the private ID in the secure database correspond to one or more medications that are already associated with the patient.

9. The computer program product of claim 7, wherein transmitting, by the first computer, the search result, further comprises at least one of the following:
 in response to identifying a duplication of the received input, from the provider, that corresponds to the private ID in the secure database, returning a collision value to the provider; and
 in response to identifying a contraindication of the received input, from the provider, with one or more inputs that correspond to the private ID in the secure database, returning a yes value to the provider.

10. The computer program product of claim 7, further comprising:
 in response to not identifying a duplication of the received input from the provider that corresponds to the private ID in the secure database and in response to not identifying a contraindication of the received input, from the provider, with one or more inputs that correspond to the private ID in the secure database, updating, by the first computer, the secure database to include the received input from the provider that corresponds to the private ID.

11. The computer program product of claim 7, further comprising:
 managing one or more medications associated with the patient, by one or more providers, using the MPC.

12. A computer system for preserving data of a patient using a cryptographic multi-party computation (MPC), the computer system comprising:
 one or more computer devices each having one or more processors and one or more tangible storage devices; and
 a program embodied on at least one of the one or more storage devices, the program having a plurality of program instructions for execution by the one or more processors, the program instructions comprising instructions for:
  receiving, by a first computer, a patient identifier from a provider, wherein the patient identifier corresponds to the patient, and wherein the first computer has a first database having an oblivious pseudo-random function (OPRF) system and a secured database having a separate private set intersection (PSI) query system, wherein the first database contains the patient identifier and a private identifier (ID), and wherein the secured database is private and stores information corresponding to the private ID;
  authenticating, by the first computer, an access by the provider;
  generating, by the first computer, a second patient identifier based on the received patient identifier;
  generating, by the first computer, the private identifier (ID) based on the received patient identifier and the generated second patient identifier by using an OPRF of the OPRF system;
  storing, by the first computer, the generated private ID in the first database;
  retrieving, by the first computer, the second patient identifier, wherein the second patient identifier corresponds to the received patient identifier, wherein the received patient identifier and the second patient identifier are different;
  receiving, by the first computer, an input from the provider that corresponds to the received patient identifier;
  accessing, by the first computer, the secure database that contains the stored private identifier (ID), wherein the stored private ID is a combination of the received patient identifier and the retrieved second patient identifier, and wherein the secure database includes data relating to the patient;
  searching, by the first computer, the secure database to obtain a search result based on the received input from the provider, by using a PSI function of the PSI system, wherein the PSI function is a cryptographic protocol that enables a two-party secure computation to obtain the search result from the secure database without a presence of a trusted third party and without revealing other information in the secure database corresponding to the private ID; and
  transmitting, by the first computer, the search result to the provider.

13. The computer system of claim 12, wherein searching, by the first computer, the secure database to obtain the search result based on the received input from the provider further comprises at least one of the following:
 identifying a duplication of the received input from the provider that corresponds to the private ID in the secure database; and
 identifying a contraindication of the received input, from the provider, with one or more inputs that correspond to the private ID in the secure database, wherein the one or more inputs that correspond to the private ID in the secure database correspond to one or more medications that are already associated with the patient.

14. The computer system of claim 12, wherein transmitting, by the first computer, the search result, further comprises at least one of the following:
 in response to identifying a duplication of the received input, from the provider, that corresponds to the private ID in the secure database, returning a collision value to the provider; and
 in response to identifying a contraindication of the received input, from the provider, with one or more inputs that correspond to the private ID in the secure database, returning a yes value to the provider.

15. The computer system of claim 12, further comprising:
 in response to not identifying a duplication of the received input from the provider that corresponds to the private ID in the secure database and in response to not identifying a contraindication of the received input, from the provider, with one or more inputs that correspond to the private ID in the secure database, updating, by the first computer, the secure database to include the received input from the provider that corresponds to the private ID.

16. The computer system of claim 12, further comprising:
  managing one or more medications associated with the patient, by one or more providers, using the MPC.

* * * * *